United States Patent
Hyun et al.

(10) Patent No.: US 10,842,842 B2
(45) Date of Patent: Nov. 24, 2020

(54) **COMPOSITION FOR PREVENTING AND TREATING OF NEUROPATHIC PAIN CONTAINING *NYPA FRUTICANS* WURMB EXTRACT**

(71) Applicant: DONG-EUI UNIVERSITY INDUSTRIAL-ACADEMIC COOPERATION FOUNDATION, Busan (KR)

(72) Inventors: Kyung-Yae Hyun, Busan (KR); Mi-Sun Kang, Yangsan-si (KR)

(73) Assignee: DONG-EUI UNIVERSITY INDUSTRIAL-ACADEMIC COOPERATION FOUNDATION, Busan (KR)

(*) Notice: Subject to any disclaimer, the term of this patent is extended or adjusted under 35 U.S.C. 154(b) by 0 days.

(21) Appl. No.: 16/562,761

(22) Filed: Sep. 6, 2019

(65) Prior Publication Data
US 2020/0222490 A1   Jul. 16, 2020

(30) Foreign Application Priority Data

Jan. 11, 2019 (KR) .................. 10-2019-0004034

(51) Int. Cl.
| | | |
|---|---|---|
| *A61K 36/00* | (2006.01) | |
| *A61K 36/889* | (2006.01) | |
| *A61K 36/13* | (2006.01) | |
| *A61K 9/00* | (2006.01) | |
| *A61K 36/78* | (2006.01) | |

(52) U.S. Cl.
CPC .......... *A61K 36/889* (2013.01); *A61K 9/0014* (2013.01); *A61K 9/0053* (2013.01); *A61K 36/00* (2013.01); *A61K 36/13* (2013.01); *A61K 36/78* (2013.01); *A61K 2236/33* (2013.01)

(58) Field of Classification Search
CPC .................................................. A61K 36/00
USPC .......................................................... 424/725
See application file for complete search history.

(56) References Cited

U.S. PATENT DOCUMENTS

2018/0344676 A1   12/2018   Hoag

FOREIGN PATENT DOCUMENTS

| KR | 10-2016-0074719 A | 6/2016 |
|---|---|---|
| KR | 10-2017-0043484 A | 4/2017 |
| KR | 10-2017-0091586 A | 7/2017 |

*Primary Examiner* — Michael V Meller
(74) *Attorney, Agent, or Firm* — Sughrue Mion, PLLC

(57) ABSTRACT

Provided are a composition for preventing and treating neuropathic pain, comprising a *Nypa fruticans* Wurmb extract, and a method of treating or preventing a neuropathic pain, comprising administering a composition comprising a *Nypa fruticans* Wurmb extract to a subject in need thereof.

4 Claims, 1 Drawing Sheet

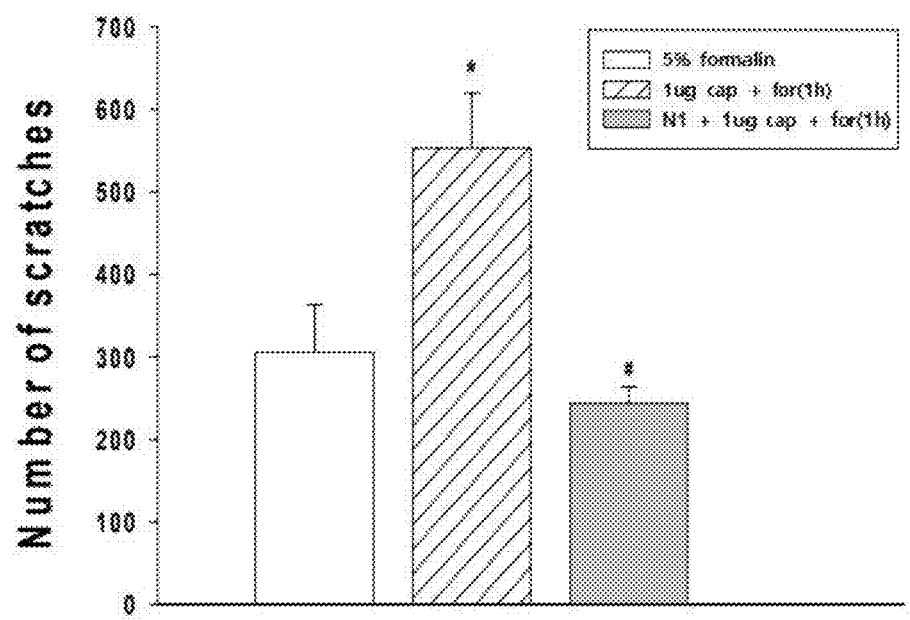

COMPOSITION FOR PREVENTING AND TREATING OF NEUROPATHIC PAIN CONTAINING *NYPA FRUTICANS* WURMB EXTRACT

CROSS-REFERENCE TO RELATED APPLICATIONS

This application is based on and claims priority from Korean Patent Application No. 10-2019-0004034, filed on Jan. 11, 2019 with the Korean Intellectual Property Office, the disclosure of which is incorporated herein in its entirety by reference.

TECHNICAL FIELD

The present disclosure relates to a composition for preventing and treating neuropathic pain, in which the composition includes *Nypa fruticans* Wurmb extract, and composition for preventing and treating neuropathic pain, in which the composition has pain relief and nerve regeneration effects and further does not cause side effects even when the dose and the administration period are increased. In addition, the present disclosure provides a method of treating or preventing a neuropathic pain, comprising administering a composition comprising a *Nypa fruticans* Wurmb extract to a subject in need thereof.

BACKGROUND

The neuropathic pain is caused by lesions or diseases of the somatosensory system, which is classified as a syndrome caused by various diseases or lesions. The neuropathic pain is a symptom of the incurable disease resulting from the nerve damage caused by physical injury, inflammation, ischemic injury, or metabolites. Clinically, there would be various symptoms: typically, allodynia, hyperalgesia, spontaneous pains, etc. Allodynia is a painful sensation caused by innocuous stimuli that do not normally provoke pain due to the abnormal sensory signal from the damaged portion. Hyperalgesia is an abnormally increased sensitivity to pain. Spontaneous pain which includes dysesthesia (spontaneous, intermittent, painless, abnormal sensation) and paresthesia (spontaneous or induced, unpleasant sensation).

The neuropathic pain is distinguished from the acute nociceptive pain caused by the discrete nervous system and sensory features, which has no therapeutic response to the standard treatment for the nociceptive pain. Generally, this is attributed to injury that has directly or indirectly influence on peripheral and central nervous systems and pathogenesis. Additionally, the sensory of the face innervated by the trigeminal nerve can even cause inflammatory pain or the neuropathic pain from diverse external stimulus.

Patients with the neuropathic pain are commonly immobile to minimize their pain, thereby lowering their mobility. Furthermore, due to chronic pain, they would be immobile for a long period, which could make their social life impossible in sever case. The majority of spinal injury patients (about 70 percent) experience the neuropathic pain within a few months after the injury, and it is worsened and become a chronic and long-lasting neuropathic pain. Moreover, as the neuropathic pain accompanies mental stress such as sleep disorder, anxiety, and depression, it not only risks the quality of patient's life but could have become serious social and economic problems for patients and their family because of catastrophic medical expenses.

In pain clinic, there are four main types of medications for the neuropathic pain inhibitor: antiepileptic drugs such as gabapentin and pregabalin, which interacts with the calcium channel; antiepileptic drugs such as carbamazepine, which interacts with sodium channel; serotonin norepinephrine reuptake inhibitors (SNRIs)-based antidepressant; and opioids that are for emergency use only.

Though most of the inhibitors are combined to treat the neuropathic pain, each medication has similar side effects. Thus, the combination not only intensifies the side effect but also impedes therapeutics effects. Because the patients commonly take the neuropathic pain inhibitor for a long time, an ideal one for prevention and treatment has low toxicity and is possible to be taken orally. Further, despite the development of various pain killer and pain-relief methods, it is reported that 75 percent of patients with the neuropathic pain is suffering from serious pain. Hence, development of pain inhibitor, medication, or food that has no toxicity and side effect and has greater painkilling effects is required to effectively treat the neuropathic pain.

Meanwhile, since Caterina et al. reported vanilloid receptor in 1997 with relative to the transient receptor potential (TRP) ion channel, there has been a growing interest in the TRP ion channels in the pain study. Transient receptor potential vanilloid 1 (TRPV1) and TRPA1 (transient receptor potential ankyrin 1) perceive noxious temperatures and mechanical stimuli and are involved in pain sensation. TRPV1 is a TRP ion channel that is activated by heat stimulation, which plays a critical role in neuropathic pain, as a main signal integrator of noxious stimulus receptor.

Capsaicin, the main compound that puts the hot in chili peppers, causes pain by activating TRPV1 receptors found in the membranes of the neurons perceiving pain and temperature. The reason why people immediately feel the burning in mouth is that capsaicin aviates TRPV1. As it has been widely known that it shows a strong irritation at first, but gradually continuous pain-relieving effects when it is used as a topical or systemic medication, numerous kinds of capsaicin derivatives have been synthesized to develop pain killer. Activation of TRPV1 is not only effective in the treatment of pain but involved in inflammation, and therefore, studies on its activation originating from natural food sources would certainly help to treat and prevent a number of diseases.

PRIOR ART DOCUMENT

Patent Literature (Patent Document 1) Korean Patent 10-2012-1132040 B1

SUMMARY

The present disclosure has been made in an effort to provide the composition for preventing and treating neuropathic pain in which the composition includes *Nypa fruticans* Wurmb extract.

The present disclosure has been made in an effort to provide the composition for preventing and treating neuropathic pain in which the composition is derived from natural materials that can alleviate neuropathic pain.

The present disclosure has been made in an effort to provide the composition for preventing and treating neuropathic pain in which the composition is free of side effects and may be used periodically or over the long term.

An exemplary embodiment of the present disclosure provides the composition for preventing and treating of neuropathic pain, in which the composition includes *Nypa fruticans* Wurmb extract.

The neuropathic pain includes a disease selected from the group consisting of central neuropathic pain and peripheral neuropathic pain.

The composition includes one inhibiting transient receptor potential vanilloid 1 (TRPV1) to exhibit antinociceptive and nerve regeneration effects.

The extract includes one extracted with an extraction solvent selected from the group consisting of water, $C_1$ to $C_6$ lower alcohols, and mixtures thereof.

Another exemplary embodiment of the present disclosure provides the functional food including the composition for preventing and treating neuropathic pain.

Yet another exemplary embodiment of the present disclosure provides the skin external preparation including the composition for preventing and treating neuropathic pain.

Still another exemplary embodiment of the present disclosure provides the medicament including the composition for preventing and treating neuropathic pain.

Hereinafter, the present disclosure is described in more detail.

The term "extract" as used herein is widely used to mean crude extracts, while a wider meaning also refers to additional materials fractionated from these extracts. That is, the extract includes not only extract obtained using the extraction solvents previously explained but also any extracts acquired by applying an additional refinement process. For instance, there is fractionation obtained by penetrating the above extracts through an ultrafilter that retains constant cut-off values for the number of molecules; another example is the differentiation based on various chromatographies (those manufactured for differentiation by size, electric charge, hydrophobicity or hydrophilicity). Also, this fractionation, which has been acquired by many different refinement procedures carried out additionally, are included in the extract of the present disclosure.

These extracts used in the present disclosure can be manufactured in a powdery state through an additional process such as vacuum distillation, freeze-drying or spray drying.

The term "neuropathic pain" as used herein refers to all pain resulting from one or more of the lesions, central nervous system and peripheral nervous system dysfunction.

The composition for preventing and treating neuropathic pain according to one embodiment of the present disclosure includes an extract of *Nypa fruticans* Wurmb as an active ingredient.

*Nypa fruticans* Wurmb is also called dani or nipa palm, and is a plant belonging to the genus *Arisaema amurense* var. *serratum*, which is cultivated on the freshwater or salty beaches of estuaries in Southeast Asia such as Myanmar, Indonesia, and the Philippines. *Nypa fruticans* Wurmb is called "Bamboo shoot from the sea" because it looks like a bamboo shoot of Korea. *Nypa fruticans* Wurmb is a plant that has traditionally been used for tooth inflammation and has recently been imported to Korea. Previous studies have shown that it contains a large amount of phenolic acid and flavonoids, and thus it has been reported that antioxidative effect and cholesterol inhibitory effect are excellent. 100 g of *Nypa fruticans* Wurmb contains 6,040 mg of polyphenol, which is 43 times higher than that of 6 years old red ginseng, 22 times higher than that of blueberries, and 41 times higher than that of Aster scaber. It has been reported that *Nypa fruticans* Wurmb includes chlorogenic acid, protocatechuic acid, and kaempferol. It is presumed that it is supposed to be excellent for controlling the inflammation. However, no specific effects and mechanisms have been studied yet. In addition, the results of studies on pain are very scarce, and in particular, the effects on the development and prevention of sciatica such as neuropathic pain have not been proven.

The neuropathic pain includes one selected from the group consisting of nerve damage, neuropathy, central neuropathic pain, and peripheral neuropathic pain.

Neuropathic pain is caused by a change in the function or structure of the nerves, and in some cases the afferent pathway is blocked or not.

The central neuropathic pain is caused by the hypothalamic syndrome and spinal cord injury stroke, and the controlling function of the peripheral nervous system is lost, resulting in an unrestrained hyperactivity of the Ad or C-afferent nerve fibers.

The peripheral neuropathy pain includes pain due to neuroma, phantom limb pain, thermoalgesia, pain associated with the sympathetic nervous system, pain due to brachial plexus injury, trigeminal neuralgia, postherpetic neuralgia, and the like. Peripheral nerves come from the brain and spinal cord and have a wide range of functions that connect many parts of the body. Peripheral nerve injury or disease may be caused by nerve damage, spinal cord and neuronal damage, of which 60 to 70% are often caused by lesions of the peripheral nerve itself. Currently injuries of traumatic peripheral nerves due to traffic accidents and industrial accidents are increasing. Pain that occurs when the peripheral nerve is compressed is caused by internal deformation of the nervous system to cause sustained pain. Further, peripheral nerve is also a tissue which is highly vulnerable to compression, and the degree of injury is closely related to the degree of pressure applied to the type of nerve tissue involved and the pressure time thereof. One of the nerve injuries which may be caused by such nerve compression is the crush injury. This is usually caused by sciatic nerve mechanical compression, causing pain and abnormal sensations with nerve distribution, resulting in severe muscle deterioration and muscle atrophy.

The composition inhibits transient receptor potential vanilloid 1 (TRPV1) to exhibit antinociceptive and nerve regeneration effects.

Transient receptor potential vanilloid 1 (TRPV1 known as a non-selective cationic channel, is activated by capsaicin which is a major hot spice of pepper, heat (>43°), acid (>pH 6) and the like, and it is one of the multifaceted nociceptors involved in various pain signal conduction. The expression of TRPV1 increases when tissue damage occurs, which plays an important role in conduction of inflammatory harmful sensations due to the sensitization. Damaged tissues release inflammatory substances such as vascular endothelial cells bradykinin, serotonin, substance P and calcitonin gene-related peptide (CGRP), prostaglandin, and histamine. The substance sensitizes the primary sensory neurons to gather surrounding immune cells into the damaged area. A series of processes leads to the release of more inflammatory substances. Formalin and capsaicin, respectively, are drugs that are widely used in pain models and cause harmful behavioral reactions (pain response) after injections on the hind legs, lips, beard and jaw joints of experimental animals. In addition, TRPV1 is known to be activated by inflammatory mediators, such as nerve growth factor, bradykinin, and the like, which are released from inflammatory sites induced by the injection of these drugs.

Accordingly, the present disclosure identifies effects of TRPV1 channel, which is activated by capsaicin injected in the facial area of white mouse on the changes in the size of inflammatory pain induced by formalin, confirming that *Nypa fruticans* Wurmb extract inhibits TRPV1 to show reduced effects on inflammation or neuropathic pain.

The present disclosure provides a composition that contains *Nypa fruticans* Wurmb extract as an active ingredient and inhibits TRPV1 to show excellent effects on inflammatory or neuropathic pain relief.

However, compared with using the *Nypa fruticans* Wurmb extract alone, when a combined extract with natural extracts, it can exhibit more excellent effects on inflammatory or neuropathic pain relief through inhibition of TRPV1.

Preferably, the natural extract may further include a natural extract selected from the group consisting of *Cephalotaxus koreana* Nakai extract, *Botrychium ternatum* Swartz. extract, *Saururus chinensis* (Lour.) Baill. extract, and mixtures thereof.

The *Cephalotaxus koreana* Nakai is an evergreen shrub that grows in mountain valleys and forests and is 3 m high. The leaves are linear and arranged in two rows, the tip is sharp, the front side is green, and the veins are sharp. The flowers are diecious and bloomed in April, the male flowers are oblate-spherical, and the female flowers hang on one by two. The fruit is round, ripened in red in August to September of next year, and the seed is long elliptical and brown.

The *Botrychium ternatum* Swartz. is *Sceptridium ternatum* (Thunb.) Lyon, which is a perennial plant that grows in sunny forests and meadows. A thick fleshy roots that spread out in all directions. Leaves are split into two pieces, and they are nutrient and fertile frond leaves. The sterile leaves have long petiole, split into three pieces, and have sawtooth on the edge. Sporophyll is longer than sterile leaf, upper part is long split, and sporangium hang on the branch.

The *Saururus chinensis* (Lour.) Baill. is a perennial plant which grows in a wetland with a height of 50 to 100 cm and a rhizome of white color. Leaves are alternate leave. The tip is sharp, the lower part is heart-shaped, and the edge is flat. The flowers are bisexual and bloom in June to August as white, and the spike grows in opposition leaves. Fruits are round and have three to five chambers. One of seeds is contained in each chamber.

The composition for preventing and treating neuropathic pain further includes a natural extract selected from the group consisting of *Cephalotaxus koreana* Nakai extract, *Botrychium ternatum* Swartz. extract, *Saururus chinensis* (Lour.) Baill. extract and the mixtures thereof in addition to *Nypa fruticans* Wurmb extract. The complex extracts are used to exhibit more excellent effects compared to the composition for preventing and treating neuropathic pain.

Preferably, the composition of the present disclosure may include 40 to 60 parts by weight of *Cephalotaxus koreana* Nakai extract, 40 to 60 parts by weight of *Botrychium ternatum* Swartz. extract, and 40 to 60 parts by weight of *Saururus chinensis* (Lour.) Baill. extract with respect to 100 parts by weight of *Nypa fruticans* Wurmb extract. When used as a complex extract within the above range, the effect of preventing and treating neuropathic pain is further improved due to the combined action of each ingredient.

The extract includes one extracted with an extraction solvent selected from the group consisting of water, $C_1$ to $C_6$ lower alcohols and mixtures thereof.

Specifically, in order to produce *Nypa fruticans* Wurmb extract, the present disclosure includes the steps of pulverizing a natural product; leaching the pulverized product using an organic solvent; after leaching, drying the sample; re-leaching the dried sample with an organic solvent; after leaching, drying the sample; leaching with water; and leaching to obtain a natural extract.

The method of producing the natural extract extracted using the organic solvent may further include the step of performing fractionation using an organic solvent.

The method for producing the extract may be a conventional extraction method such as an ultrasonic extraction method, a leaching method, and a reflux extraction method. Specifically, it may be an extract obtained by extracting a natural product from which foreign substances have been removed by washing and drying with water, an alcohol having 1 to 6 carbon atoms, or a mixed solvent thereof and an extract obtained by sequentially applying the solvents to a sample.

The reflux extraction method is carried out under the condition of, based on 100 mL of water or an alcohol having 1 to 6 carbon atoms, 10 to 30 g of a pulverized natural product, 1 to 3 hours of refluxing time, and 50 to 100% of an alcohol having 1 to 6 carbon atoms or water. More specifically, based on 100 mL of an alcohol having 1 to 6 carbon atoms or 100 mL of water, it is carried out under the condition of 10 to 20 g of a pulverized natural product, 1 to 2 hours of refluxing time and 70 to 90% of an alcohol having 1 to 4 carbon atoms or water.

The leaching method is carried out at 15 to 30° C. for 24 to 72 hours, and water or 50 to 100% of an alcohol having 1 to 6 carbon atoms is used as an extraction solvent. More specifically, the method is carried out at 20 to 25° C. for 30 to 54 hours, and the extraction solvent is water or an alcohol having 70 to 80% of an alcohol having 1 to 6 carbon atoms.

The ultrasonic extraction method is carried out by reacting at 30 to 50° C. for 0.5 to 2.5 hours, and the extraction solvent is water or 50 to 100% of an alcohol having 1 to 6 carbon atoms. Specifically, the extraction is carried out at 40 to 50° C. for 1 to 2.5 hours, and water or 70 to 80% of an alcohol having 1 to 6 carbon atoms is used as the extraction solvent.

The extraction solvent may be used in an amount of 2 to 50 times, more preferably 2 to 20 times, based on the weight of the sample. For the extraction, the sample can be left in the extraction solvent for 1 to 72 hours and more specifically for 24 to 48 hours for leaching.

After the extraction, the extract may be fractionated by sequentially applying new fraction solvents. The fraction solvent used for fractionation includes at least one selected from the group consisting of water, hexane, butanol, ethyl acetic acid, ethyl acetate, methylene chloride, and mixtures thereof, preferably ethyl acetate or methylene chloride.

An additional method such as concentration or freeze-drying may be used after the extract or fraction is obtained.

The functional food according to another embodiment of the present disclosure may include the composition for preventing and treating neuropathic pain.

The composition for preventing and treating neuropathic pain of the present disclosure includes *Nypa fruticans* Wurmb extract. When it is used as a functional food composition, there is a problem that the degree of preference is lowered due to seaweed-specific odor. Likewise, even in the case of a complex extract obtained by mixing *Nypa fruticans* Wurmb extract with natural extracts, when it is provided as a functional food composition, there is a problem that the degree of preference is lowered due to the taste and aroma inherent to the natural extract mixed with the seaweed-specific odor.

To address the issue, more preferably, the present disclosure may further include a *Pachysandra terminalis* extract and a *Siraitia grosvenorii* extract in order to improve the palatability.

The *Pachysandra terminalis* grows in the shade of a tree, the main stem hangs sideways, the tip is straight and green, and initially there are fine hairs but the fine hairs gradually disappear. It grows up to about 30 cm in height. Leaves are alternate, but they are gathered in the upper part and look like an inverted egg, and the upper part has sawtooth. There are fine hairs on the leaf surface veins, and the lower part becomes narrowed to become petiole. Further, flowers bloom in April or May and are white and hang in a spike. The female flower hangs slightly under the flower head, and the male flower mostly hangs on the upper part. The calyx is divided into four pieces, and there are no petals. The stamen is divided into three to five, and the style is divided into two pieces and is tilted. The fruit is a drupe egg-shaped and has no hairs on the surface. It is distributed in Korea, Japan, Sakhalin Island, and China.

*Siraitia grosvenorii* is an herbaceous perennial plant of gourds and is native to China and Thailand. The fruits and leaves of *Siraitia grosvenorii* are used as medicinal substances in oriental medicine. They are mainly grown in highland areas with foggy, cool, sunny and well-drained, and inhabited in soils with a lot of humic substances. Thus, it is difficult to cultivate artificially because of difficult cultivation conditions. So, they have long been used as valuable medicines.

*Pachysandra terminalis* extract and *Siraitia grosvenorii* extract are further included to neutralize the specific taste and aroma of natural extract and the seaweed-specific odor, thereby providing a functional food composition having excellent palatability.

Preferably, the composition of the present disclosure may include, with respect to 100 parts by weight of *Nypa fruticans* Wurmb extract, 40 to 60 parts by weight of *Cephalotaxus koreana* Nakai extract, 40 to 60 parts by weight of *Botrychium ternatum* Swartz. extract, 40 to 60 parts by weight of *Saururus chinensis* (Lour.) Baill. extract, 20 to 30 parts by weight of *Pachysandra terminalis* extract and 30 to 50 parts by weight of *Siraitia grosvenorii* extract. When used as a complex extract within the above range, it exhibits an excellent effect of preventing and treating neuropathic pain, while providing a functional food composition having excellent palatability.

The term "functional food" as defined herein means food prepared or processed using raw materials or ingredients having useful functions in the human body according to the Korean Health Functional Foods Act No. 6727, and "functional" means the intake for the purpose of controlling nutrients or of obtaining useful effects on health use such as physiological action for the structure and function of the human body.

When the extract according to the present disclosure is used as a food additive, the extract may be added alone, used in combination with other food or food ingredients, and suitably used according to a conventional method. Examples of the food to which the above substances may be added include meats, sausage, bread, chocolate, candies, snacks, confectioneries, pizza, ramen, other noodles, gums, dairy products including ice cream, various soups, beverages, tea, drinks, alcoholic beverages, vitamin complexes and the like. Examples of the food include healthy foods in a conventional sense.

The skin external preparation according to another embodiment of the present disclosure may include the composition for preventing and treating neuropathic pain.

The medicament according to another embodiment of the present disclosure may include the composition for preventing and treating neuropathic pain.

The desired dosage of the extract according to the present disclosure varies depending on the condition and the weight of the patient, the degree of disease, the type of drug, the route of administration and the period of time, and it may be appropriately selected by those skilled in the art. However, for the desired effect, the extract is preferably administered at a dosage of 0.01 mg/kg to 10 g/kg per day, preferably 1 mg/kg to 1 g/kg per day. The administration may be carried out once a day or divided into several doses a day. Therefore, the dosage does not limit the scope of the present disclosure in any way.

According to the exemplary embodiments of the present disclosure, the composition for the prevention and treatment of neuropathic pain derived from the present disclosure may alleviate neuropathic pain.

According to the exemplary embodiments of the present disclosure, when the composition for the prevention and treatment of neuropathic pain is used, it is possible to use the extract derived from a natural material to provide an excellent relaxing effect for neuropathic pain without side effect. Thus, it may be used for irregular neuropathic pain periodically or for a long period of time.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 shows a neuropathic pain model test result of a composition according to one embodiment of the present disclosure.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, embodiments of the present disclosure are described in detail so that those skilled in the art can easily carry out the present disclosure. However, the present disclosure may be embodied in many different forms and is not limited to the embodiments described herein.

Preparation Example: Preparation of Extract

1. Preparation of *Nypa fruticans* Wurmb Extract 100 g of dry pulverized *Nypa fruticans* Wurmb extract was mixed with 1 L of 80% ethanol at −20° C., and the extraction was carried out at room temperature for 4 hours. After the extraction, a filter cake was used to remove the powder component, and only the liquid component was filtered through the flask. The filtered liquid component was boiled in a water bath at 65° C. to produce pure *Nypa fruticans* Wurmb extract (N1).

2. Preparation of Other Natural Extracts 1 kg of the original sample of the dry pulverized *Cephalotaxus koreana* Nakai extract in a powder form was added to 30% ethanol, and the reflux extraction was performed at 80° C. for 1 to 3 hours. The extraction was repeated twice at the same times and at the same period, and the obtained extract was dried under reduced pressure and then vacuum dried at 60° C. to prepare *Cephalotaxus koreana* Nakai extract (N2).

*Botrychium ternatum* Swartz. extract (N3), *Saururus chinensis* (Lour.) Baill. extract (N4), *Pachysandra terminalis* extract (X1) and *Siraitia grosvenorii* extract (X2) were prepared using the same method as the preparation method of *Cephalotaxus koreana* Nakai extract (N2).

3. Preparation of Complex Extract

The *Nypa fruticans* Wurmb extract (N1), *Cephalotaxus koreana* Nakai extract (N2), *Botrychium ternatum* Swartz. extract (N3), *Saururus chinensis* (Lour.) Baill. extract (N4), *Pachysandra terminalis* extract (X1) and *Siraitia grosvenorii* extract (X2) were mixed in the weight range as shown in the following Table 1 to prepare a composition for preventing and treating neuropathic pain.

TABLE 1

|    | G1  | G2  | G3  | G4  | G5  | G6  | G7  | G8  | G9  |
|----|-----|-----|-----|-----|-----|-----|-----|-----|-----|
| N1 | 100 | 100 | 100 | 100 | 100 | 100 | 100 | 100 | 100 |
| N2 | —   | 30  | 40  | 60  | 80  | 30  | 40  | 60  | 80  |
| N3 | —   | 30  | 40  | 60  | 80  | 30  | 40  | 60  | 80  |
| N4 | —   | 30  | 40  | 60  | 80  | 30  | 40  | 60  | 80  |
| X1 | —   | —   | —   | —   | —   | 10  | 20  | 30  | 40  |
| X2 | —   | —   | —   | —   | —   | 30  | 40  | 50  | 60  |

(Unit: parts by weight)

Experimental Example 1: Neuropathic Pain Relief Effect of *Nypa fruticans* Wurmb Extract The formalin test a representative experimental model for evaluating the inflammatory pain behavior response through injured tissue and inflammatory reaction caused by subcutaneously injecting formalin into the facial surface of mouse. Capsaicin, an activator of TRPV1, can be additionally injected to evaluate neuropathic pain behavior response.

The specific experimental method is described below. The experimental animals were adapted for at least 10 minutes in a laboratory plastic container before evaluation of their pain response. 25 µl of 5% formalin was injected using an insulin syringe (0.25×8 mm), and they were observed to regain consciousness within a few seconds after the injection of formalin. First, to examine the effect of TRPV1 channel activity on the behavior response of formalin-injected experimental animals, the pain behavior responses caused by capsaicin alone at a concentration of 0.1 µg/10 µL, 1 µg/10 µL, 10 µg/10 µL injected through an inserted polyethylene tube were observed in the same manner as after the formalin injection. Next, the pain behavior responses were observed for 45 minutes after injection of capsaicin at a concentration of 0.1 µg/10 µL and 1 µg/10 µL on the same injection site one hour before the formalin injection. The solvent (vehicle) of capsaicin was a mixture of 10% ethanol and physiological saline.

It was known that before the formalin injection, 0.1 µg/10 µL and 1 µg/10 µL capsaicin was pretreated to show a significant increase in prominent pain behavior response, indicating that the TRPV1 channel activated by capsaicin injected into the face of the white mouse affected the change in the degree of formalin-induced neuropathic pain. Then, in order to examine relief effect of *Nypa fruticans* Wurmb extract on neuropathic pain, 500 mg/kg *Nypa fruticans* Wurmb extract (N1) was treated 10 minutes before the injection of capsaicin to observe effects on the change of neuropathic pain behavior response (See FIG. 1).

As a result, it was found that the treatment of *Nypa fruticans* Wurmb extract (N1) significantly alleviated the increased pain behavior response. It was known that the TRPV1 channel increased neuropathic pain sensation by capsaicin, and *Nypa fruticans* Wurmb extract (N1) significantly reduced this hyperpathia.

Experimental Example 2: Comparison of Results of Pain Tests for Complex Extract

1. Capsaicin Pain Model Test for Complex Extract

It was confirmed that the N1 had effects of preventing and treating neuropathic pain through experiment of neuropathic pain model for the N1.

Thereafter, the same experiments were conducted on G2 to G5, and the results are described as index with G1 for the purpose of making a relative comparison. The degree of effect of G1 is set to index 5, and the degree of effect of G2 to G5 is expressed as an index of 1 to 10. The higher the number, the better the pain control effect.

TABLE 2

|                        | G1 | G2 | G3 | G4 | G5 |
|------------------------|----|----|----|----|----|
| neuropathic pain model | 5  | 3  | 4  | 5  | 7  |

(Unit: index)

Table 2 above shows the relative comparison results of the pain control effects of G2 to G5 compared to G1. Compared with G1, G3 and G4 showed equivalent pain control effects, whereas G5 showed relatively good pain control effects.

Experimental Example 3: Sciatic Nerve Regeneration Effect Due to TRPV1 Expression Reduced by *Nypa fruticans* Wurmb Extract 1. Induction of Crushing Injury on the Sciatic Nerve 15 mg/100 g ketalar (ketarnin hydrochloride) of Yuhan was intraperitoneally injected to general anesthesia. Then, the hairs from both femurs were removed. Then, the operating field was sterilized with 10% betadine solution. Surgery was performed in the conventional manner under the aseptic operation. After the sciatic nerve was exposed, and the crushing injury was caused for 30 seconds on spot which was 1 cm above rams between the tibial nerve and the total peroneal nerve using hemostatic forceps with 1 mm diameter at the tip. For the analysis of the results, in order to easily recognize the crush area at the time of nerve cutting, the muscles and skin were sutured after ligation with 7-Osilk loosely to the injured area of the epineurium.

2. Evaluation of the Effects of *Nypa fruticans* Wurmb Extract on Nerve Regeneration Experimental animals were divided into experimental group (n=15) and control group (n=15). Animals of the experimental group were administered with 500 mg/kg *Nypa fruticans* Wurmb extract (N1) and divided into 1 week-administered group, 2 week-administered group and 3 week-administered group in which five animals were assigned to each group. Animals of the control group were administered with physiological saline and divided into 1 week-administered group, 2 week-administered group and 3 week-administered group in which five animals were assigned to each group. After the end of each experiment by time, the animals in which the experiment was completed were anesthetized, and then the sciatic nerve was excised and the histomorphological changes were observed by optical microscope and electron microscope.

As a result, the number of total myelinated nerve fibers in the experimental group treated with *Nypa fruticans* Wurmb extract (N1) changed to 36.0±3.4, 154.3±33.8 and 129.3±12.7, respectively at 1 week, 2 weeks and 3 weeks after administration, and the number of total myelinated nerve fibers tends to be increased rapidly ($p<0.01$) between 1 and 2 weeks but decreased slightly at 3 weeks. The control group administered with physiological saline tends to be gradually increased from 35.3±9.1, 74.3±9.6, and 116.0±15.1 at 1 week, 2 weeks and 3 weeks, respectively. The number of degenerated myelinated nerve fiber of the control group were 38.3±8.5, 40.7±15.0 and 36.3±8.5 at 1 week, 2 weeks and 3 weeks, respectively. Therefore, it was found that the administration of *Nypa fruticans* Wurmb extract (N1) after crushing injury to the sciatic nerve reduced the degenerated myelinated nerve fibers produced by the crush injury and recovered the myelinated nerve fibers.

TABLE 3

|  | 1 week | 2 weeks | 3 weeks |
|---|---|---|---|
| Experimental group administered with N1 | 36.0 ± 3.4 | 154.3 ± 33.8 | 129.3 ± 12.7 |
| Control group administered with physiological saline | 35.3 ± 9.1 | 74.3 ± 9.6 | 116.0 ± 15.1 |

Experimental Example 4: Preference Test

1. Sensuality Evaluation Test

G1, G5 Of complex extracts, and G6 to G9 of fermentation complex extracts were diluted to prepare the tea. The tea was tasted by 10 tasting persons, and the taste and aroma were represented by an index of 1 to 10. The average value (0.5 rounded) was shown in the following Table 4. The higher the number of the index, the higher the preference.

TABLE 4

|  | G1 | G5 | G6 | G7 | G8 | G9 |
|---|---|---|---|---|---|---|
| Taste | 5.5 | 4.5 | 6 | 6 | 6 | 5 |
| Aroma | 4.5 | 2.5 | 4 | 5 | 6 | 4 |
| Complex preference (average) | 5.5 | 4 | 5.5 | 6 | 6.5 | 5 |

(Unit: index)

Referring to Table 4, the taste of *Nypa fruticans* Wurmb extract in G1 was evaluated to be good, but the aroma peculiar to the seaweeds reduced the degree of preference. The G5 mixture added the sour aroma to reduce the degree of preference. In addition, the G9 mixture increased bitter and sour aroma to reduce the degree of preference. On the other hand, it was confirmed that the specific aroma and taste of *Nypa fruticans* Wurmb extract was neutralized by the complex extracts G7 and G8 to enhance the degree of preference.

Therefore, the complex extracts G7 and G8 may provide the functional food having effects for relieving neuropathic pain having aroma and taste with higher preference.

The preferred embodiments of the present disclosure have been described in detail hereinabove, but the scope of the present disclosure is not limited to the above embodiments. Various modifications and improvements of the present disclosure using the basic concept of the present disclosure by the skilled person in the art, which is defined by the following appended claims, also falls within the scope of the present disclosure.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of treating a human suffering from a spinal cord injury consisting essentially of administering a therapeutically effective amount of an extract of *Nypa fruticans* Wurmb and an extract selected from the group consisting of *Cephalotaxus koreana* Nakai extract, *Sceptridium tematum* (Thunb.) Lyon extract, *Saururus chinensis* (Lora.) Bail, extract and mixtures thereof to the human in need thereof to effectively treat the spinal cord injury in the human.

2. The method according to claim 1, wherein the human suffering from the spinal cord injury also suffers from nerve damage, neuropathy, central neuropathic pain or peripheral neuropathic pain.

3. The method according to claim 1, wherein the method inhibits transient receptor potential vanilloid 1 (TRPV1) to exhibit antinociceptive and nerve regeneration effects in the human suffering from the spinal cord injury.

4. The method according to claim 1, wherein the *Nypa fruticans* Wurmb is extracted with a solvent selected from the group consisting of water, $C_1$ to $C_6$ lower alcohols, and mixtures thereof.

* * * * *